(12) United States Patent
Sugiyama

(10) Patent No.: US 8,702,833 B2
(45) Date of Patent: Apr. 22, 2014

(54) HEALTH FOOD

(75) Inventor: Chikatsugu Sugiyama, Miyagi (JP)

(73) Assignee: Nihon Pack Co., Miyagi (JP)

( * ) Notice: Subject to any disclaimer, the term of this patent is extended or adjusted under 35 U.S.C. 154(b) by 304 days.

(21) Appl. No.: 13/309,682

(22) Filed: Dec. 2, 2011

(65) Prior Publication Data
US 2012/0076873 A1 Mar. 29, 2012

Related U.S. Application Data

(62) Division of application No. 11/632,419, filed as application No. PCT/JP2005/012891 on Jul. 13, 2005, now abandoned.

(30) Foreign Application Priority Data

Jul. 14, 2004 (JP) ................................ 2004-207261

(51) Int. Cl.
C05F 11/02 (2006.01)
C05B 17/02 (2006.01)

(52) U.S. Cl.
USPC .......................... 71/24; 71/34; 71/49; 71/50

(58) Field of Classification Search
USPC ...................... 71/11–27, 34, 49, 50
See application file for complete search history.

(56) References Cited

U.S. PATENT DOCUMENTS

| | | | |
|---|---|---|---|
| 2,797,985 A * | 7/1957 | Larson | 71/8 |
| 4,743,287 A | 5/1988 | Robinson | |
| 4,949,459 A | 8/1990 | Noble | |
| 5,997,602 A * | 12/1999 | Aijala | 71/28 |
| 6,613,366 B1 | 9/2003 | Fitzpatrick | |
| 8,110,017 B2 * | 2/2012 | Wells | 71/11 |
| 2004/0126458 A1 | 7/2004 | Lee | |

FOREIGN PATENT DOCUMENTS

| | | |
|---|---|---|
| JP | 56-11783 | 2/1981 |
| JP | 4-121158 | 4/1992 |
| JP | 4-141056 | 5/1992 |
| JP | 5-105565 | 4/1993 |

(Continued)

OTHER PUBLICATIONS

Asakura Publishing Company Limited, "Encyclopedia of Botanical Nutrients and Manure", May 10, 2002, with partial English translation.

(Continued)

*Primary Examiner* — Wayne Langel
(74) *Attorney, Agent, or Firm* — Wenderoth, Lind & Ponack, L.L.P.

(57) ABSTRACT

The object of the present invention is to consume raw food cultivated in appropriate soil.
The constitution of the health food is: consuming cereals including rices and wheats with or without husk, millets, pulses, tubers, leaf vegetables, fruit vegetables, rosette crops, root vegetables, citrus fruits, fruits, melons, seaweeds, and liverworts etc. as is; or consuming powders thereof, or by soaking in water so as to process to a degree that cell are not destructed (or if cells are destructed, the whole of leaf vegetables including root, stem, and leaf or a portion thereof are consumed as e.g. juice) and consuming without processing treatment including heating, boiling in water, or steaming; or these cereals, millets, or pulses are soaked in water to allow sprouting, and consumed at around the time of sprouting without processing treatment including heating, boiling in water, or steaming.

12 Claims, 3 Drawing Sheets

(56) References Cited

FOREIGN PATENT DOCUMENTS

| | | |
|---|---|---|
| JP | 11-9199 | 1/1999 |
| JP | 2000-125803 | 5/2000 |
| JP | 2000-143828 | 5/2000 |
| JP | 2002-125620 | 5/2002 |
| JP | 3095748 | 5/2003 |
| JP | 2003-235508 | 8/2003 |
| JP | 2003-339344 | 12/2003 |
| WO | 02/34755 | 5/2002 |

OTHER PUBLICATIONS

International Search Report issued Oct. 18, 2005 in International Application No. PCT/JP2005/012891.
Shigeru Sawayama, "Analyzing Taste, Food Material and Processing, Basic Knowledge of Prune and Method for Using the Same", Science of Cooking, vol. 70, No. 848, pp. 140-142, Jun. 5, 2004.
Oxford English Dictionary, definition of "crop", second edition, 1989, accessed online by Examiner on Dec. 14, 2010.

* cited by examiner

AR Inhibitory Activity

Sample

1    Rokkaku-reishi mushroom (malted rice)

| ul/well | PBS | Et | Me | HPBS |
|---|---|---|---|---|
| 0 | 100 | 100 | 100 | 100 |
| 0.01 | 104 | 92 | 96 | 80 |
| 0.1 | 112 | 92 | 76 | 76 |
| 1 | 64 | 100 | 68 | 52 |
| 10 | 20 | 16 | 8 | 16 |

2    Ancient Black Rice (asamurasaki) (malted rice)

| ul/well | PBS | Et | Me | HPBS |
|---|---|---|---|---|
| 0 | 100 | 100 | 100 | 100 |
| 0.01 | 116 | 104 | 68 | 100 |
| 0.1 | 116 | 88 | 72 | 96 |
| 1 | 72 | 44 | 8 | 52 |
| 10 | 40 | 8 |  | 16 |

3    Nippon-suginishiki 515 cultivated using Aquagen enzyme (malted rice)

| ul/well | PBS | Et | Me | HPBS |
|---|---|---|---|---|
| 0 | 100 | 100 | 100 | 100 |
| 0.01 | 96 | 84 | 80 | 92 |
| 0.1 | 80 | 96 | 84 | 80 |
| 1 | 100 | 84 | 84 | 84 |
| 10 | 180 | 0 | 16 | 20 |

HEALTH FOOD

This application is a divisional of U.S. application Ser. No. 11/632,419, filed Feb. 25, 2008 now abandoned, which is a national stage application of International application No. PCT/JP2005/012891, filed Jul. 13, 2005.

TECHNICAL FIELD

The present invention relates to a health food which ameliorates disease of a body and builds a healthy body. Specifically, the invention relates to a health food which builds a body that suppresses intractable diseases such as diabetes.

BACKGROUND ART

Conventionally, various products have been proposed as health food. For example, Japanese Patent No. 3019261 entitled "Raw Vegetable Health Food" (Patent document 1) discloses a health food composed of a combination of raw vegetables and uncooked brown rice with addition of common salt.

Further, in particular, diabetes which is considered an intractable disease often induces complications such as arteriosclerotic angiopathy. It is therefore necessary in treatment of diabetes to maintain good nutritional and health conditions and to acquire resistance against various diseases. The following products have been recently proposed as such health food.

For example, in Japanese Patent Application Laid-Open No. 2003-189803 (Patent document 2), cooked rice is proposed in which a health pharmaceutical having medicinal properties is applied onto the surface of brown rice, etc. to produce traditional medicinal rice, which is cooked by ordinary method. Further, in Japanese Patent Application Laid-Open No. H09-40566 (Patent document 3), fermentation product of lactic acid bacteria obtained from a mixture of rice bran and powdered brown rice is known. In Patent document 4, it is known to use brown rice germ as a substrate, and this is mixed with reishi mushroom, the mixture is heat-treated, inoculated, and then cultured.

Patent document 1: Japanese Patent No. 3019261, pp. 1
Patent document 2: Japanese Patent Application Laid-Open No. 2003-189803, pp. 1
Patent document 3: Japanese Patent Application Laid-Open No. H09-40566, pp. 1
Patent document 4: Japanese Patent Application Laid-Open No. 2002-29994, pp. 1

DISCLOSURE OF THE INVENTION

Problems to be Solved by the Invention

Patent document 1 shows consuming of raw vegetable and brown rice generally cultivated in ordinary soil, but the nitrogen component absorbed from the soil cannot be ingested enough.

The traditional medicinal rice of Patent document 2 was made by applying a health component onto the surface of brown rice etc., cooked, and consumed, and processing of brown rice was troublesome. Further, Patent document 3 describes a product where fermentation product of lactic acid bacteria is added to rice such as brown rice, and relates to immunoadjuvant. In addition, Patent document 4 shows processing of brown rice etc., in which brown rice etc. is steamed, this is inoculated and mixed together with e.g. reishi mushroom.

The present invention provides for improvement on conventionally problematic food such as cereals which have harmful effects on human body and for food that builds a healthy body.

In particular, the present invention provides for a health food with the primary objective to consume without steaming or heating, and without processing treatment of the surface of, for example, cereals including rice (brown rice, wet-field rice, dry-field rice, ancient rice, fragrant rice, etc.) and wheat (wheat, barley, oat, etc.); millets including Italian millet, Chinese millet, buckwheat, Indian corn, Japanese millet, corn, and sweet corn; or pulses including sesame, soybean, black bean, adzuki bean, and kidney bean; tubers including sweet potato, potato, Jerusalem artichoke, black sweet potato, Chinese yam, Japanese taro, Japanese yam, and Caiapo; rosette crops; melons; fruit vegetables; root vegetables; citrus fruits; and fruits.

Another object of the present invention is to provide for a health food, in which it is important that the health food is not digested and absorbed in the small intestine, but rather digested in the small intestine, degraded in the large intestine and absorbed into the body.

The object of the present invention is to provide for a health food suitable for the body, in particular suitable for diabetes, which do not go through the process of heating or steaming of, for example, uncooked cereals, millets, and pulses, or these foods without husk.

Means for Solving the Problems

The present invention comprises the following constitution to achieve the above objects.

The constitution of the health food is: rices, cereals, millets, pulses, tubers, leaf vegetables, fruit vegetables, citrus fruits, melons, fruits, rosette crops, and root vegetables, or rices, cereals, millets, and pulses with or without husk are consumed as is; or dried or powdered product soaked in water, and consumed as a whole without processing treatment including heating, boiling in water, and steaming, or dried, powdered, and consumed; or, for the cereals, millets, or pulses, soaked in water to allow sprouting, and consumed at around the time of sprouting without processing treatment including heating, boiling in water, or steaming.

The above described object of the present invention can be achieved by a health food comprising the constitution of consuming grains of the cereals, millets, pulses, tubers, fruit vegetables, leaf vegetables, seeds, citrus fruits, fruits, green vegetables, or root vegetables of consuming as is, or consuming powdered grain, in which one or more of 2 to 3 kinds of these grains are consumed in a size suitable as food, but not limited by size; or the constitution of consuming the cereals, millets, and pulses in beta-starch state, and allowing degradation by digestive fluid within esophagus, stomach, and small intestine, fermentation and degradation by enteric bacteria within large intestine, and digestion and absorption.

In addition, the above described object of the present invention can be achieved by a health food in which cereals including rices and wheats or millets with or without husk; pulses including sesame, soybean, black bean, adzuki bean, and kidney bean; tubers including sweet potato, potato, Jerusalem artichoke, and black sweet potato; fruit vegetables; or root vegetables, are produced in a soil, in which agricultural chemicals including insecticide, bactericide, and antibiotic or inorganic synthetic materials such as synthetic food, synthetic additive, and chemical fertilizer remain in a small amount, essentially do not remain, in which fungi, microorganisms, and insects can coexist with the food chain, and in which organic fertilizer that does not use e.g. the above described agricultural chemicals is added, and consumed as is, or consumed powders thereof or soaked in water, or consumed as a whole, or dried, powdered, and consumed; or, for the cereals, millets and/or pulses, soaked in water and consumed when sprouted or at around the time of sprouting.

The health food of the present invention is a great shift from conventional views on food. In other words, it is a health food which can maintain health of the body to have resistance against pathogens by a small amount of food. Particularly, it is important that it is consumed raw as is, digested in the small intestine, and degraded and absorbed in the large intestine.

As used in the present invention, consuming as a whole means that in case of vegetables, consuming not just the leaf part, but the entirety including the stem and root parts. For example, in case of eggplant, it means consuming the entirety of vine, stem, and fruit. By consuming the entirety, it is possible to ingest well-balanced nutrients.

The minimal condition is to produce and cultivate cereals, millets, pulses, tubers, citrus fruits, fruits, melons, leaf vegetables, fruit vegetables, and root vegetables etc. by its natural state in nature in soil without using any inorganic agricultural chemicals etc.

It is well known that consuming uncooked cereals, millets, and pulses directly as grains results in chewing well in the mouth, leading to strengthening of the jaw and activation of the brain. In addition, it is said that in the case of cereals and millets at around the time of sprouting, gamma-aminobutyric acid (GABA) increases to build a healthy body.

When the cereals, pulses, vegetables, citrus fruits, fruits, melons, leaf vegetables, fruit vegetables, and root vegetables etc. of the present invention cannot be consumed raw, it may be powdered and consumed dispersed in water. In addition, it can be consumed delectably when it is made into cereal juice or soup, by mixing not just one but multiple kinds of cereals.

Foods that can be used in the health food of the present invention are, but not limited to, many kinds of food including the above described cereals including rices such as wet-field rice, dry-field rice, ancient wild rice, and fragrant rice, and wheats including wheat, barley, and oat; or millets including Italian millet, Chinese millet, buckwheat, Indian corn, and Japanese millet; or pulses including sesame, soybean, black bean, adzuki bean, and kidney bean; tubers including sweet potato, potato, Jerusalem artichoke, and black sweet potato; citrus fruits; fruits; melons; leaf vegetables; fruit vegetables; or root vegetables.

For example, the above described cereals including rices including wet-field rice, dry-field rice, ancient wild rice, fragrant rice and wheats including as wheat, barley, and oat, with husk, and cereals without husk;

millets including Italian millet, Japanese millet, Chinese millet, buckwheat, Indian corn, corn, and sweet corn, or seeds including walnut;

pulses such as sesame, soybean, black bean, adzuki bean, kidney bean, green pea, and favabean;

tubers including sweet potato, potato, Jerusalem artichoke, Japanese taro, Chinese yam, Japanese yam, Caiapo, and dasheen;

vegetables such as green onion, green perilla, perilla, green asparagus, parsley, wormwood, rapeseed, and cinnamon;

leaf vegetables such as qing-geng-cai, komatsuna, leek, spinach, Jew's mallow, lettuce, Chinese cabbage, and cabbage;

root vegetables such as Japanese radish, lotus root, turnip, onion, burdock, Japanese ginger, sugar beet, carrot, shallot, and Japanese horseradish;

fruit vegetables such as pumpkin, gourd, cucumber, and eggplant fruits such as apple, loquat, peach, Japanese persimmon, and grape;

citrus fruits such as tangerine, kumquat, lemon, and kabosu;

melons such as watermelon, Oriental melon, and melon;

liverwort such as lichens, mosses, and liverworts;

seaweeds such as kelp and hijiki;

Good results are obtained when not just one but several kinds of these are mixed together with the above described food and consumed raw.

In the health food of the present invention, cereals, millet, pulses etc. may be consumed as is, but for those who are unaccustomed, may be powdered and dispersed in water for consumption. When these cereals are heated, vitamin and enzyme are broken down, protein is denatured, and fat is oxidized, and degraded into glucose in the small intestine and absorbed into the body, causing weight gain.

When the cereals, etc. are consumed in a sprouted state or at around the time of sprouting, the degradation cycle of sprouted brown rice in the body is as shown in FIG. 1. Starch, hemicellulose etc. are turned into from hexose to pyruvic acid, degraded by enteric bacteria in the large intestine, and become nutritional component of the body.

Fermentation and degradation are carried out by enzyme and bacteria in the large intestine, degrade fat into short-chain fatty acid. Regarding this process, according to the theory by Mitsuo Kouda, it is said that it will be as shown in FIG. 1.

The flow of the short-chain fatty acid is as follows. Starch, cellulose, and hemicellulose of the cereals etc. are turned into hexose and pentose, then via pyruvic acid into short-chain fatty acid including acetic acid, butyric acid, propionic acid, and valeric acid, which are used for growth of enteric bacteria flora. These are absorbed in the large intestine and become energy. Indole and skatole are excreted in stool. On the other hand, hydrogen, methane, and carbon dioxide gases produced are excreted but are partly absorbed into the blood and exhaled. As such, when it is turned into short-chain fatty acids, energy is produced within the body and the body becomes greatly enduring.

The health food of the present invention is preferably consumed to 80% or 60% fullness. When consumed on an empty stomach, peristaltic movement within the intestine is activated and motilin, a digestive hormone, is secreted as a hormone to excrete the content of the intestine when the stomach is empty. Peristaltic movement of the intestine becomes active, and occurrence of cancer is significantly reduced by facilitating the excretion of the content of the intestine and stercoral.

According to the health food of the present invention, blood sugar level and amount of insulin generally tend to rise in the body after eating cooked rice. Blood sugar level tend to decrease over time by eating the health food of the present invention comprising brown rice (stercoral in particular is dissolved).

As such, even in diabetes patients, increase in blood sugar level does not occur following ingestion of the health food of the present invention.

Generally, when millets are heated, steamed, or cooked, beta-starch is converted into alpha-starch and absorbed in the small intestine.

However, meals from these are absorbed in the large intestine to make a subject healthy. Beta-starch is not degraded in the small intestine, but is degraded by digestive fluid in the large intestine, and fermented and degraded by bacteria in the intestine. The fermentation and degradation is presumed to be by short-chain fatty acid cycle described below.

The health food of the present invention cannot be cultivated by production in conventional soil. In other words, in ordinary soil, residual nitrogen cycle as shown in FIG. 1 is carried out, and is therefore unsuitable.

On the other hand, the soil for cultivating the health food of the present invention has the components as shown in Table 3, resulting in decrease by half of residual nitrogen content.

|  |  | Residual nitrogen |  | Residual nitrogen |
|---|---|---|---|---|
| Komatsuna | Purchased at a supermarket | 150 mg | Cultivated in the soil of the present invention | 75 mg |
| Spinach | Purchased at a supermarket | 750 mg | Cultivated in the soil of the present invention | 300 mg |
| Shirona | Purchased at a supermarket | 750 mg | Cultivated in the soil of the present invention | 300 mg |

The method for measuring the amount of residual nitrogen was as follows.

Five grams of leaves are ground, 145 cc of distilled water was added, and stirred well. This was filtered through filter paper, and test paper was soaked in the filtrate obtained. After 1 second, it was measured in a measuring device. The calculated value was multiplied by 3 to obtain the amount of residual nitrogen in 100 g.

Fertilizers conventionally used were not appropriate for plants such as cereals, and in the pursuit of savouriness, cereals harmful to the body are produced. In particular, alpha-starch was ingested due to processing treatment such as heating and boiling in water.

In addition, with respect to the fertilizer used, agricultural chemical, antibiotic, and compound aiming to exterminate damages by disease and pest have harmful effects on the human body, causing bodies to be nonresistant to diseases.

The soil for cultivating the health food of the present invention is a soil where conditions as shown in Table 3 are maintained. In particular, it is more preferred that it is closer to the central value.

In other words, it is a soil in which residual amount of agricultural chemicals including insecticide, bactericide, and antibiotic or inorganic synthetic materials such as synthetic food, synthetic additive, and chemical fertilizer is small, essentially a soil in which there is no residual amount, a soil in which fungi, microorganisms, and insects can coexist with the food chain, and a soil in which organic fertilizer that does not use e.g. the above described agricultural chemicals is added.

Millets that do not sprout produce by chemical fertilizer and agricultural chemical have broken DNA, highly acidic and highly autoimmune plant which is a dead material has high concentration of amino acids, and results in a plant resistant to pests.

For an organic fertilizer, it is more effective to mix photosynthetic bacteria into the soil. By the addition of photosynthetic bacteria, proliferation of filamentous bacteria which is a pathogen of rice cultivation etc. is suppressed and Actinomyces is proliferated. The Actinomyces has the function to kill filamentous bacteria.

In the brown rice etc. used in the health food of the present invention, a more preferable brown rice can be produced by using plant activating enzyme "Aquagen" (the registered trademark of Nihon Pack Co.). This "Aquagen" is a plant fermentation seasoning developed based on natural materials. It is fermented with Aspergillus oryzae to bring forth the innate ability of the plant for "further activation of photosynthesis", so that the immunity of plant is increased, the concentration of amino acids is increased, and innate flavor of the plant is brought forth. When immunity is increased, the plant becomes resistant to damages by disease and pest, and regeneration of cells is reinforced, so that if the plant is eaten by bugs the same portion will regenerate.

Further, chitin goes through the plant cell wall to bind to specific protein, delivered to nuclear DNA, synthesis of mRNA, RNA, and protein on which dormant DNA acts increases, immunity is increased, chitinase is secreted to protect the cell when contacted by pathogens and pests, and immunocyte prevents invasion from the outside.

In addition, when it is converted into DNA, the substance for immune strength is ingested from the plant, so the insects can share, as well as the plant changes itself into where virus does not enter. Accordingly, a suitable plant can be cultivated without using conventional agricultural chemical or chemical fertilizer.

In this way, photosynthesis of plant is enhanced and increase in yield of high quality plant is expected.

Cereals such as rice and wheat and millets used for the health food of the present invention are cultivated in soil containing high concentrations of amino acid. When chitosan is applied to soil during growth of these plants, resistance against pests is increased, and regeneration efficiency is also good.

Moreover, the water applied to soil is preferably strong electrolyzed water. The strong electrolyzed water is superior in bactericidal effect. The strong electrolyzed water is produced by adding sodium chloride or potassium to water, electrolyzing the aqueous sodium chloride, and collecting electrolyzed strong acidic water from the anodic electrode side and at the same time strong alkaline water is produced at the cathode side.

The strong electrolyzed water includes strong acidic water of pH 3 or less (substantially 2.7 or less) and strong alkaline water of pH 11.5 (substantially 12 or more), and these strong electrolyzed waters are not a replacement of agricultural chemical as bactericide. They are more or less a preventive agent, and are not effective when disease has developed.

Rice culture regions of the world have a temperature of above a certain degree. The regions have temperature of 36° C. in 3 months or more and have high precipitation. The absorption of water of plants in this region is approximately 70%, which is adapted to water content of human body 70%. On the other hand, wheat culture regions such as Europe have temperature and precipitation inferior to rice culture regions, and it is said that water content of plants in the wheat culture regions is 30%. The plants of the regions are adapted to these natural phenomena. Accordingly, humans adapt to plants and resulted in the present food culture. In addition, when the necessary water does not exist, photosynthesis cannot be carried out and satisfactory food does not grow. This results in decrease in immune strength and vulnerability to pests.

Advantages of the Invention

According to the health food of the present invention, because cereals, millets etc. are consumed raw so it is easy to consume, and they can be powdered and consumed raw for easy consumption and easy digestion, so that they can be easily served. In addition, powder of the cereals etc. can be dispersed in water for consumption as juice or soup.

By consuming it raw, it is fermented and degraded enteric bacteria in the large intestine, and then absorbed.

BEST MODE FOR CARRYING OUT THE INVENTION

Figure 1:
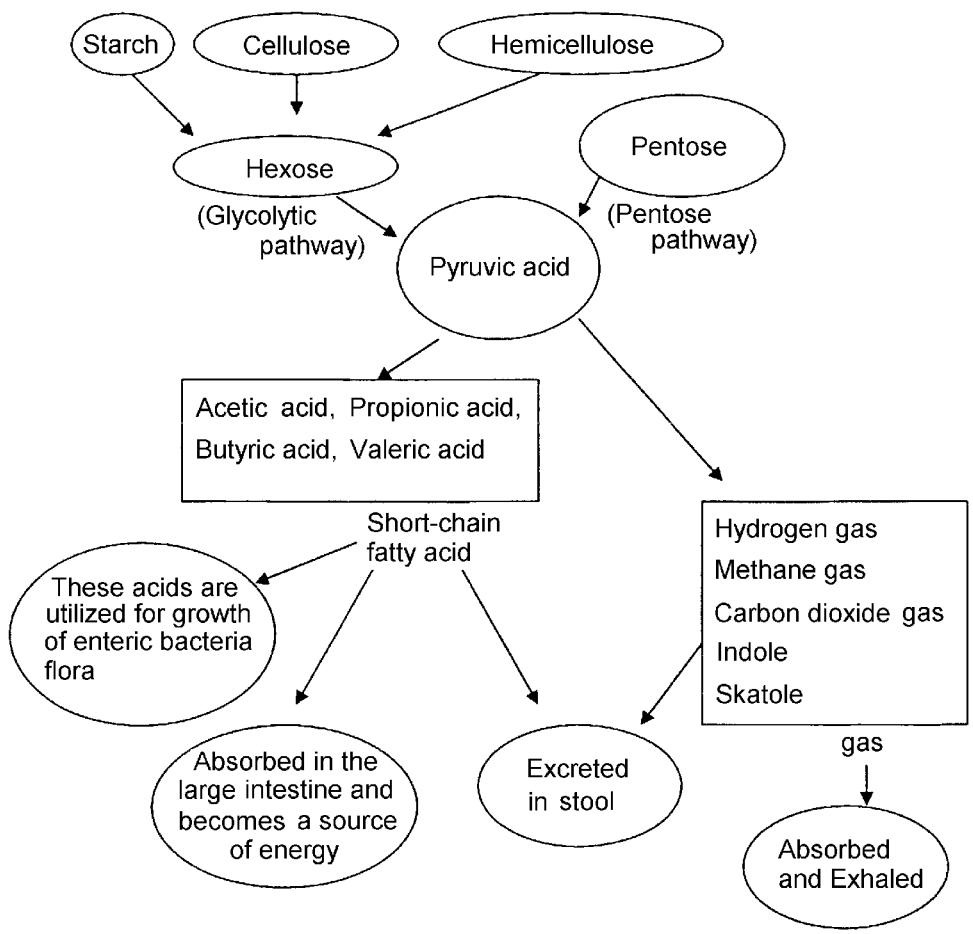
FIG. 1 shows a short-chain fatty acid cycle in the body.
Figure 2:
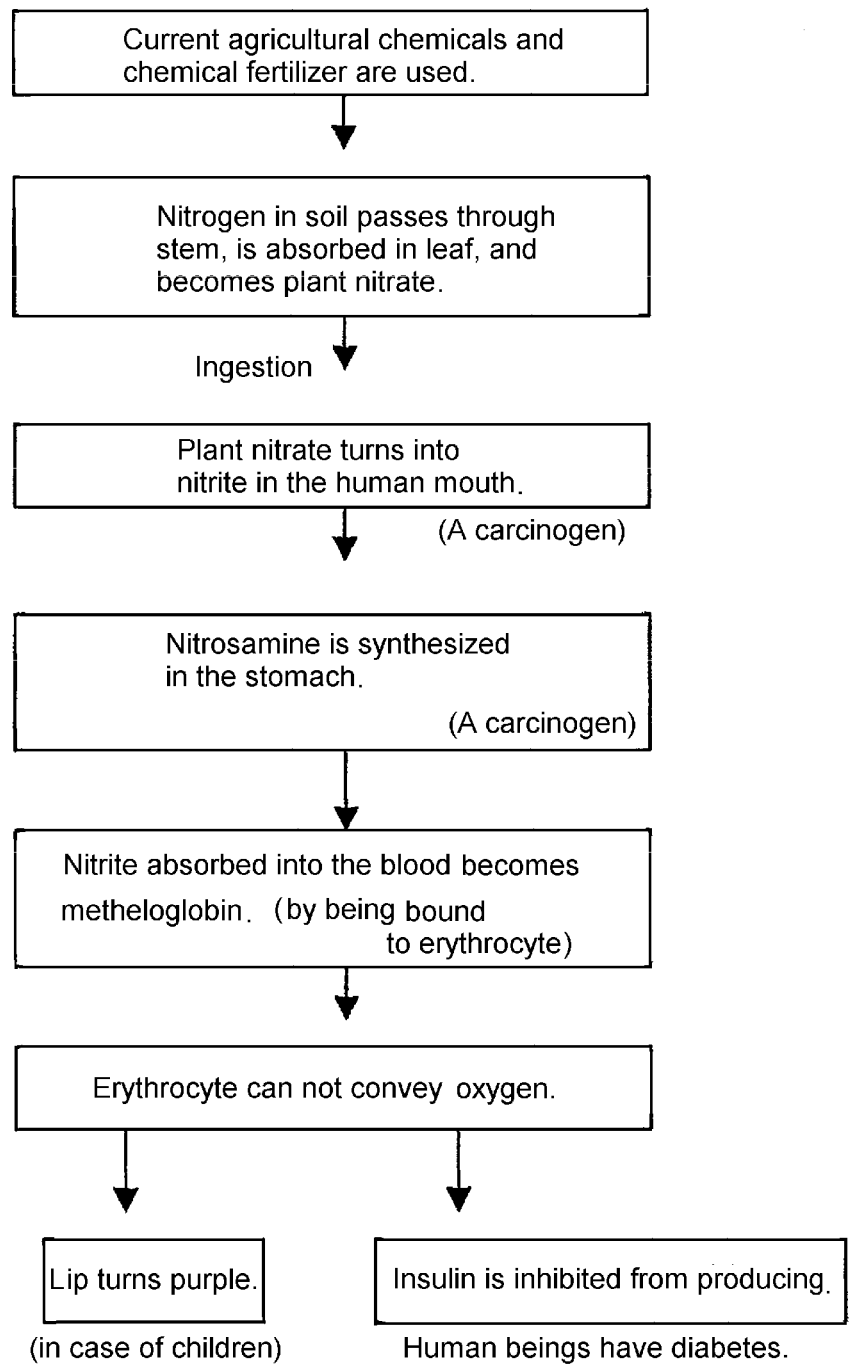
FIG. 2 shows a cycle of residual nitrogen ingested from vegetables etc.
Figure 3:
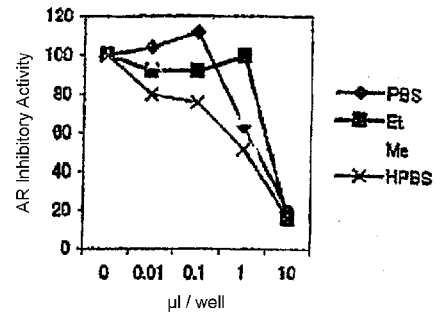
FIG. 3 shows a comparison of aldose reductase (AR) inhibitory activity in samples.
Figure 3:
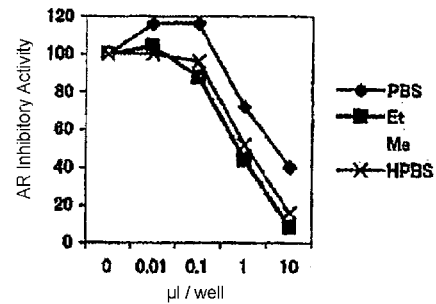
Figure 3:
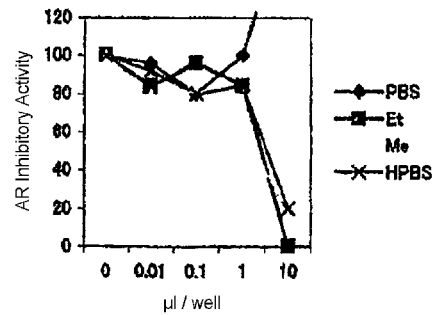

The health food of the present invention will now be described.

The cereals, millets, pulses, tubers, leaf vegetables, fruit vegetables, citrus fruits, melons, fruits, rosette crops, root vegetables, seaweeds, seeds or liverwort used in the health food of the present invention are cultivated in a soil in which residual amount of agricultural chemicals including insecticide, bactericide, and antibiotic or inorganic synthetic materials such as synthetic food, synthetic additive, and chemical fertilizer is small, essentially a soil in which there is no residual amount, a soil in which fungi, microorganisms, and insects can coexist with the food chain, using organic fertilizer that does not use e.g. the above described agricultural chemicals.

In particular, soil used for cultivating the cereals, millets, pulses, tubers, leaf vegetables, fruit vegetables, citrus fruits, melons, fruits, rosette crops, root vegetables, liverwort, seaweeds or seeds of the health food of the present invention is preferably a soil in which naturally occurring leaf mold is the main component. Cereals etc. grown in such soil contain starch etc. different from those of conventional starch, which is superior in degradation of sugar within the body.

Because starch contained in cereals, millets, and pulses without heat processing etc. is beta-starch, it is degraded by enteric bacteria in the large intestine, turned into short-chain fatty acid such as butyric acid and valeric acid, absorbed and becomes a source of energy.

Sprouted brown rice of AKITAKOMACHI cultivated in such a soil was compared with sprouted brown rice by conventional method in measurement of degree of growth. Results are shown in Table 1 below.

Table 1 shows that AKITAKOMACHI from conventional soil had 21 unsprouted grains even after 72 hours in rice incubator (water temperature 32° C.).

On the other hand, in the case of HITOMEBORE rice from the soil component shown in Table 3 of the present invention, there were no grains which did not sprout after 72 hours in the same rice incubator (water temperature 32° C.). In other words, all of the brown rice sprouted.

TABLE 1-1

① Produced in 2003/Kakizaki/AKITAKOMACHI/rice incubator (sprouted at water temperature 32° C.)

| 2003 Number of Grains | Kakizaki AKITAKOMACHI Thickness (mm) | Allowed to sprout for 0 hour Width (mm) | Length (mm) | Kakizaki AKITAKOMACHI Thickness (mm) | Allowed to sprout for 24 hours Width (mm) | Length (mm) | Kakizaki AKITAKOMACHI Thickness (mm) | Allowed to sprout for 48 hours Width (mm) | Length (mm) | Kakizaki AKITAKOMACHI Thickness (mm) | Allowed to sprout for 72 hours Width (mm) | Length (mm) |
|---|---|---|---|---|---|---|---|---|---|---|---|---|
| 1 | 2.04 | 2.84 | 5.14 | 2.21 | 2.82 | 5.38 | Maximum 2.12 | Maximum 2.86 | Maximum 6.40 | Maximum 2.12 | Maximum 3.31 | Maximum 5.61 |
| 2 | 2.12 | 2.78 | 4.90 | 2.25 | 2.86 | 5.39 | 2.18 | 2.92 | 5.75 | 2.30 | 3.15 | 6.50 |
| 3 | 2.04 | 2.73 | 5.02 | 2.29 | 2.48 | 5.32 | 2.24 | 2.97 | 5.81 | 2.16 | 2.95 | 5.85 |
| 4 | 2.00 | 2.76 | 5.11 | 2.20 | 2.98 | 5.08 | 2.22 | 2.91 | 5.65 | 2.38 | 2.85 | 6.65 |
| 5 | 1.89 | 2.36 | 4.89 | 2.10 | 2.79 | 5.16 | 2.22 | 3.37 | 5.58 | 2.24 | 3.00 | 5.30 |
| 6 | 2.16 | 2.59 | 5.06 | 2.30 | 2.24 | 5.35 | 2.19 | 3.27 | 5.63 | 2.21 | 2.96 | 5.54 |
| 7 | 2.04 | 2.71 | 5.06 | 2.30 | 2.20 | 5.02 | 2.15 | 3.07 | 5.62 | 2.18 | 3.00 | 5.27 |
| 8 | 1.95 | 2.69 | 4.77 | 2.23 | 2.77 | 5.14 | 2.10 | 2.95 | 5.10 | 2.30 | 3.30 | 6.10 |
| 9 | 1.98 | 2.82 | 5.07 | 2.80 | 3.05 | 4.87 | 2.15 | 3.13 | 5.89 | 2.15 | 3.11 | 5.43 |
| 10 | 2.17 | 2.78 | 5.09 | 2.24 | 2.88 | 5.72 | 2.30 | 3.07 | 5.51 | 2.17 | 2.97 | |
| 11 | 1.93 | 2.83 | 5.09 | 2.18 | 2.88 | 5.54 | 2.20 | 2.90 | 5.67 | | | |
| 12 | 2.17 | 2.85 | 5.10 | 2.38 | 2.84 | 5.33 | | | | | | |
| 13 | 1.98 | 2.65 | 5.06 | 2.10 | 2.72 | 4.51 | | | | | | |
| 14 | 2.09 | 2.73 | 5.36 | 2.33 | 2.58 | 5.43 | | | | | | |
| 15 | 2.10 | 2.87 | 5.12 | 2.13 | 2.79 | 5.35 | | | | | | |
| 16 | 1.98 | 2.78 | 5.02 | 2.20 | 3.26 | 5.32 | | | | | | |
| 17 | 2.04 | 2.72 | 5.11 | 2.41 | 2.85 | 5.39 | Minimum 2.16 | Minimum 2.60 | Minimum 5.02 | Minimum 2.08 | Minimum 2.88 | Minimum 4.74 |
| 18 | 2.13 | 2.66 | 5.26 | 2.19 | 2.30 | 5.80 | 2.16 | 2.57 | 5.34 | 2.30 | 2.53 | 5.23 |
| 19 | 2.15 | 2.37 | 5.64 | 2.08 | 3.10 | 5.24 | 2.06 | 2.45 | 5.57 | 2.19 | 2.72 | 4.90 |
| 20 | 2.17 | 2.89 | 5.82 | 2.41 | 3.00 | 5.64 | 2.15 | 2.72 | 5.39 | 2.07 | 3.05 | 5.45 |
| 21 | 1.94 | 2.73 | 4.83 | 2.27 | 2.63 | 5.16 | 2.10 | 2.83 | 5.10 | 2.07 | 2.47 | 5.85 |
| 22 | 1.95 | 2.75 | 4.84 | 2.24 | 3.12 | 5.26 | 2.23 | 2.90 | 5.27 | 2.10 | 2.89 | 5.45 |
| 23 | 1.93 | 2.78 | 4.88 | 2.32 | 2.95 | 5.34 | 1.96 | 2.71 | 5.29 | 2.23 | 2.21 | 4.95 |
| 24 | 2.07 | 2.70 | 4.79 | 2.28 | 2.65 | 5.31 | 2.30 | 3.07 | 5.17 | 2.03 | 2.65 | 4.91 |
| 25 | 2.16 | 2.67 | 4.93 | 2.18 | 2.80 | 5.29 | 2.34 | 2.73 | 5.51 | 2.04 | 2.49 | 5.24 |
| 26 | 2.15 | 2.59 | 4.91 | 2.43 | 2.93 | 4.96 | 2.08 | 2.69 | 5.42 | 2.27 | 2.81 | 5.37 |
| 27 | 1.99 | 2.87 | 4.96 | 2.22 | 2.66 | 5.54 | | | | | | |
| 28 | 2.05 | 2.85 | 5.12 | 2.09 | 3.00 | 5.73 | | | | | | |
| 29 | 1.93 | 2.74 | 4.94 | 2.30 | 2.86 | 5.18 | | | | | | |
| 30 | 2.07 | 2.90 | 5.07 | 2.22 | 2.82 | 5.29 | Average 2.18 | Average 2.89 | Average 5.51 | Average 2.18 | Average 2.87 | Average 5.50 |
| 31 | 2.02 | 2.58 | 4.99 | 2.25 | 3.07 | 5.32 | Weight (110 grains) | Sprouted 70 grains | Not sprouted 40 grains | Weight (110 grains) | Sprouted 89 grains | Not sprouted 21 grains |
| 32 | 2.09 | 2.71 | 5.27 | 2.14 | 2.95 | 5.23 | 2.4 g | | | 2.5 g | | |
| 33 | 2.07 | 2.70 | 4.79 | 2.39 | 3.10 | 5.21 | 1 grain 0.022 | | | 1 grain 0.023 | | |
| 34 | 2.05 | 2.75 | 5.38 | 2.15 | 3.02 | 5.24 | | | | | | |
| 35 | 2.20 | 2.74 | 4.82 | 2.21 | 3.05 | 5.04 | | | | | | |
| 36 | 2.10 | 2.46 | 5.33 | 2.22 | 2.81 | 5.25 | | | | | | |
| 37 | 1.98 | 2.93 | 5.00 | 2.14 | 2.81 | 5.11 | | | | | | |
| 38 | 1.93 | 2.90 | 4.87 | 2.27 | 2.90 | 5.29 | | | | | | |
| 39 | 2.11 | 2.75 | 5.05 | 2.37 | 2.98 | 5.64 | | | | | | |
| 40 | 1.99 | 2.71 | 5.02 | 2.50 | 2.35 | 5.78 | | | | | | |
| 41 | 2.05 | 2.59 | 4.81 | 2.43 | 2.91 | 5.07 | | | | | | |
| 42 | 1.97 | 2.57 | 4.87 | 1.84 | 2.96 | 5.24 | | | | | | |

TABLE 1-1-continued

① Produced in 2003/Kakizaki/AKITAKOMACHI/rice incubator (sprouted at water temperature 32° C.)

| 2003 Number of Grains | Kakizaki AKITAKOMACHI Thickness (mm) | Allowed to sprout for 0 hour Width (mm) | Length (mm) | Kakizaki AKITAKOMACHI Thickness (mm) | Allowed to sprout for 24 hours Width (mm) | Length (mm) | Kakizaki AKITAKOMACHI Thickness (mm) | Allowed to sprout for 48 hours Width (mm) | Length (mm) | Kakizaki AKITAKOMACHI Thickness (mm) | Allowed to sprout for 72 hours Width (mm) | Length (mm) |
|---|---|---|---|---|---|---|---|---|---|---|---|---|
| 43 | 2.01 | 2.61 | 4.75 | 2.10 | 3.04 | 5.35 | | | | | | |
| 44 | 1.99 | 2.61 | 5.11 | 2.40 | 2.75 | 4.74 | | | | | | |
| 45 | 2.10 | 2.68 | 4.81 | 2.35 | 3.07 | 5.54 | | | | | | |
| 46 | 2.01 | 2.72 | 5.17 | 2.30 | 3.12 | 5.61 | | | | | | |
| 47 | 1.98 | 2.81 | 5.26 | 2.22 | 2.77 | 5.26 | | | | | | |
| 48 | 2.06 | 2.80 | 5.16 | 2.17 | 2.89 | 5.41 | | | | | | |
| 49 | 2.02 | 2.65 | 4.94 | 2.20 | 2.92 | 5.56 | | | | | | |
| 50 | 1.96 | 2.81 | 4.69 | 2.53 | 3.39 | 5.50 | | | | | | |
| 51 | 2.17 | 2.80 | 5.03 | 2.57 | 3.05 | 5.30 | | | | | | |
| 52 | 2.11 | 2.64 | 5.23 | 2.31 | 2.99 | 5.53 | | | | | | |
| 53 | 1.96 | 2.70 | 5.50 | 2.32 | 2.93 | 5.28 | | | | | | |
| 54 | 2.02 | 2.96 | 5.09 | 2.32 | 2.84 | 5.53 | | | | | | |
| 55 | 2.02 | 2.76 | 5.20 | 2.35 | 2.90 | 5.38 | | | | | | |
| 56 | 2.11 | 2.41 | 5.04 | 2.50 | 2.95 | 5.54 | | | | | | |

TABLE 1-2

① Produced in 2003/Sasaki/HITOMEBORE/rice incubator (sprouted in water temperature 32° C.)

| 2003 Number of Grains | Sasaki HITOMEBORE Thickness (mm) | Allowed to sprout for 0 hour Width (mm) | Length (mm) | Sasaki HITOMEBORE Thickness (mm) | Allowed to sprout for 24 hours Width (mm) | Length (mm) |
|---|---|---|---|---|---|---|
| 1 | 2.12 | 2.23 | 5.30 | Maximum | Maximum | Maximum |
| 2 | 2.15 | 2.81 | 5.22 | 2.28 | 3.27 | 6.23 |
| 3 | 2.22 | 2.61 | 4.80 | 2.25 | 3.05 | 6.03 |
| 4 | 2.28 | 2.78 | 5.02 | 2.30 | 3.25 | 6.02 |
| 5 | 2.06 | 2.78 | 4.93 | 2.31 | 2.95 | 6.03 |
| 6 | 2.11 | 2.98 | 5.20 | 2.32 | 3.10 | 5.91 |
| 7 | 2.23 | 2.84 | 4.99 | 2.31 | 3.18 | 6.05 |
| 8 | 2.27 | 2.86 | 4.80 | 2.33 | 3.10 | 6.14 |
| 9 | 2.20 | 2.84 | 5.14 | 2.29 | 3.07 | 5.53 |
| 10 | 2.03 | 2.74 | 4.90 | 2.32 | 2.95 | 6.70 |
| 11 | 2.07 | 2.89 | 5.05 | 2.35 | 3.03 | 6.14 |
| 12 | 2.10 | 2.95 | 4.62 | | | |
| 13 | 2.12 | 2.89 | 4.86 | | | |
| 14 | 2.15 | 2.75 | 5.53 | | | |
| 15 | 2.04 | 2.63 | 5.02 | | | |
| 16 | 2.20 | 2.62 | 4.85 | | | |
| 17 | 2.15 | 2.94 | 5.14 | Minimum | Minimum | Minimum |
| 18 | 1.92 | 2.54 | 4.98 | 2.10 | 2.90 | 5.23 |
| 19 | 2.08 | 2.56 | 5.49 | 2.27 | 2.88 | 5.40 |
| 20 | 2.08 | 2.99 | 4.65 | 2.26 | 3.12 | 4.98 |
| 21 | 2.03 | 2.71 | 5.23 | 2.19 | 3.13 | 4.98 |
| 22 | 2.20 | 2.93 | 5.25 | 2.04 | 3.02 | 5.12 |
| 23 | 1.98 | 2.93 | 5.11 | 2.28 | 3.11 | 4.70 |
| 24 | 2.03 | 2.69 | 5.52 | 2.10 | 3.15 | 5.32 |
| 25 | 1.98 | 2.93 | 5.28 | 2.30 | 2.97 | 4.90 |
| 26 | 2.12 | 2.52 | 4.92 | 2.03 | 3.00 | 4.87 |
| 27 | 2.04 | 2.98 | 5.53 | 2.20 | 2.88 | 4.88 |
| 28 | 2.10 | 3.31 | 5.11 | | | |
| 29 | 1.95 | 2.81 | 4.71 | | | |
| 30 | 1.99 | 2.64 | 5.02 | Average | Average | Average |
| 31 | 2.16 | 2.83 | 5.04 | 2.24 | 3.06 | 5.56 |
| 32 | 1.86 | 2.97 | 5.08 | | | |
| 33 | 1.93 | 2.88 | 5.11 | Weight (110 grains) | Sprouted | Not sprouted |
| 34 | 2.23 | 2.78 | 5.32 | 2.85 | 100 grains | 10 grains |
| 35 | 2.04 | 2.87 | 4.91 | 1 grain | | |
| 36 | 2.00 | 2.64 | 5.09 | 0.026 | | |
| 37 | 2.20 | 2.71 | 4.71 | | | |
| 38 | 2.14 | 2.79 | 4.98 | | | |
| 39 | 2.15 | 2.88 | 5.12 | | | |
| 40 | 2.25 | 2.84 | 4.65 | | | |
| 41 | 2.11 | 2.96 | 5.13 | | | |
| 42 | 2.31 | 2.81 | 4.93 | | | |
| 43 | 2.19 | 2.81 | 5.28 | | | |
| 44 | 2.08 | 2.80 | 4.65 | | | |
| 45 | 2.06 | 2.42 | 4.92 | | | |
| 46 | 2.02 | 2.75 | 4.96 | | | |
| 47 | 1.97 | 2.72 | 5.11 | | | |
| 48 | 2.18 | 3.05 | 5.23 | | | |
| 49 | 2.14 | 3.09 | 5.07 | | | |
| 50 | 2.18 | 2.71 | 5.02 | | | |
| 51 | 2.05 | 3.01 | 4.82 | | | |
| 52 | 2.09 | 2.32 | 5.31 | | | |
| 53 | 2.10 | 2.59 | 4.86 | | | |
| 54 | 2.04 | 2.86 | 4.67 | | | |
| 55 | 2.05 | 2.74 | 4.81 | | | |
| 56 | 2.15 | 2.88 | 5.19 | | | |

| 2003 Number of Grains | Sasaki HITOMEBORE Thickness (mm) | Allowed to sprout for 48 hours Width (mm) | Length (mm) | Sasaki HITOMEBORE Thickness (mm) | Allowed to sprout for 72 hours Width (mm) | Length (mm) |
|---|---|---|---|---|---|---|
| 1 | Maximum | Maximum | Maximum | Maximum | Maximum | Maximum |
| 2 | 2.28 | 3.00 | 5.58 | 2.30 | 2.86 | 6.28 |
| 3 | 2.31 | 3.21 | 5.85 | 2.34 | 3.15 | 6.00 |
| 4 | 2.23 | 2.02 | 5.65 | 2.35 | 3.10 | 5.65 |
| 5 | 2.28 | 3.10 | 6.19 | 2.36 | 2.90 | 6.20 |
| 6 | 2.32 | 3.24 | 6.35 | 2.35 | 2.80 | 5.79 |
| 7 | 2.34 | 3.35 | 5.81 | 2.33 | 2.90 | 5.75 |
| 8 | 2.29 | 3.10 | 5.91 | 2.21 | 3.25 | 5.41 |

TABLE 1-2-continued

① Produced in 2003/Sasaki/HITOMEBORE/rice incubator (sprouted in water temperature 32° C.)

| | | | | | | |
|---|---|---|---|---|---|---|
| 9 | 2.27 | 2.92 | 6.02 | 2.25 | 3.35 | 6.38 |
| 10 | 2.29 | 3.10 | 6.03 | 2.28 | 3.04 | 6.00 |
| 11 | 2.35 | 3.15 | 5.75 | 2.29 | 3.20 | 6.04 |
| 12 | | | | | | |
| 13 | | | | | | |
| 14 | | | | | | |
| 15 | | | | | | |
| 16 | | | | | | |
| 17 | Minimum | Minimum | Minimum | Minimum | Minimum | Minimum |
| 18 | 2.29 | 3.20 | 5.60 | 2.29 | 2.85 | 4.98 |
| 19 | 2.29 | 3.29 | 5.27 | 2.29 | 2.80 | 5.53 |
| 20 | 2.05 | 2.90 | 4.70 | 2.05 | 2.65 | 5.95 |
| 21 | 2.04 | 2.70 | 5.56 | 2.04 | 2.86 | 4.75 |
| 22 | 2.40 | 2.95 | 5.43 | 2.40 | 2.47 | 6.45 |
| 23 | 2.15 | 2.94 | 4.82 | 2.15 | 2.64 | 5.42 |
| 24 | 2.18 | 3.01 | 5.39 | 2.18 | 2.72 | 5.39 |
| 25 | 2.36 | 3.02 | 5.06 | 2.36 | 2.97 | 5.43 |
| 26 | 2.18 | 2.80 | 5.19 | 2.18 | 2.92 | 5.32 |
| 27 | 2.27 | 2.43 | 5.71 | 2.27 | 2.93 | 4.98 |
| 28 | | | | | | |
| 29 | | | | | | |
| 30 | Average | Average | Average | Average | Average | Average |
| 31 | 2.26 | 2.97 | 5.59 | 2.26 | 2.92 | 5.69 |
| 32 | | | | | | |
| 33 | Weight (110 grains) | Sprouted | Not sprouted | Weight (110 grains) | Sprouted | Not sprouted |
| 34 | 2.9 g | 105 grains | 5 grains | 3 g | 110 grains | 0 grains |
| 35 | 1 grain | | | 1 grain | | |
| 36 | 0.264 | | | 0.027 | | |

As shown in Tables 1-1 and 1-2, as compared to cultivation in conventional soil, it is apparent that rice resistant to disease is cultivated in the soil for cultivating the health food of the present invention.

Additionally, results of analysis of components of common white rice, sprouted brown rice, and sprouted brown rice from the soil of the present invention (by Japan Food Research Laboratories) are shown below.

TABLE 2

| Article analyzed | Content in the sprouted brown rice of the Present Invention | Content in common sprouted brown rice | Content in white rice |
|---|---|---|---|
| Iron | 1.64 mg/100 g | 1.56 mg/100 | 1.15 mg/100 g |
| Calcium | 15.6 mg/100 | 17.7 mg/100 | 8.1 mg/100 |
| Potassium | 163 mg/100 | 135 mg/100 | 11.2 mg/100 |
| Magnesium | 137 mg/100 | 132 mg/100 | 12.5 mg/100 |
| Zinc | 1.91 mg/100 | 2.06 mg/100 | 1.23 mg/100 |
| Inositol | 211 mg/100 | 212 mg/100 | 12 mg/100 |
| Dietary Fiber | 2.8 g/100 | 2.7 g/100 | 0.5 g/100 |
| Phytic Acid (mesoinosit hexaphosphate) | 840 mg/100 | 831 mg/100 | n.d. |
| Free Gamma-Amino Acid | 13 mg/100 | 24 mg/100 | n.d. |
| Total Ferulic Acid | 24 mg/100 | 23 mg/100 | 5.4 mg/100 |

Note:
Methods of measurement
Iron: o-phenanthroline absorption spectrometry,
Calcium: ICP spectrometry,
Potassium, magnesium, and zinc: atomic absorption spectrometry,
Inositol: bioassay
Dietary fiber: enzyme-weight assay,
Phytic acid: vanadomolybdic acid absorption spectrometry
Free gamma-aminobutyric acid: amino acid automatic analysis
Total ferulic acid: high performance liquid chromatography Effects that cannot be expected from conventional soil are achieved by the soil for cultivating the cereals etc. of the health food of the present invention.

The range of appropriate level of components of the nutrients of this soil (100 g of soil) is as follows.

TABLE 3

| Article analyzed | Appropriate range | |
|---|---|---|
| Acidity (pH) | 3.2~5.5~7.5 | |
| Electroconductivity | 0.02~0.05~5 | |
| Nitrogen | | |
| Nitrogen content of amino acids (A-N) | 0.02~0.3~50 | mg |
| (N-N) | 0.02~0.7~70 | mg |
| Phosphate in available form | 2~15~400 | mg |
| Exchangeable potassium | 1~15~300 | mg |
| Absorbance index of phosphate | 40~500~3000 | mg |
| Exchangeable lime (Calcium) | 50~200-1000 | mg |
| Exchangeable magnesia (Magnesium) | 5~35~400 | mg |
| Manganese in available form | 0.5~5~70 | PPM |
| Iron in available form | 1.5~15~300 | PPM |
| Copper in available form | 0.1~1~30 | PPM |
| Zinc in available form | 1.5~10~80 | PPM |
| Boron | 0.5~2~30 | PPM |
| Molybdenum | 0.002~0.05~2 | PPM |
| Humus | 1.0~9.0% | |
| Capacity of base substitution | 5~40 | CDC |

By cultivating the cereals etc. of the present invention in soil containing the components shown in Table 3, health food can be ingested.

In the leaves of cereals cultivated in the soil of the present invention, 300 mg or less of residual nitrogen was normal.

However, when cultivated in soil using inorganic chemical fertilizer and agricultural chemical of the conventional method, spinach had residual nitrogen of 800 to 1600 mg.

Because residual nitrogen is said to have harmful effects on the human body, the less is the better. Residual nitrogen in plant leaves transforms into nitrate, turns into nitrite (a carcinogen) in the human mouth, and turns into nitrosamine (a carcinogen) in the stomach. When the nitrosamine is absorbed into the blood, it turns into metheloglobin, binds to erythrocytes, and disables delivery of oxygen. This causes suppression of insulin production and causes the subject to be susceptible to diabetes. When delivery of oxygen by erythrocytes is decreased, the subject becomes oxygen-deprived. Children will have purple lips.

The method of measuring the amount of residual nitrogen was as follows.

Five grams of leaves are ground, and 145 cc of distilled water was added. This was filtered through filter paper, and test paper was soaked in the filtrate for 1 second. The number obtained as measured by chromatography was multiplied by 3 to obtain the amount of residual nitrogen in 100 g.

To describe about sprouted brown rice among the cereals of the present invention, by cultivating in the soil described above, amino acid based on nucleic acids of natural organic matter is reinforced due to photosynthesis by sunlight, dormant enzyme is activated, gamma-amino acid (GABA) is accumulated in the sprouted portion, and active ingredient of brown rice increases, so that it contains more tai-nutrient than unsprouted brown rice. GABA is known to activate the blood stream and to have a function to facilitate metabolism.

Uncooked brown rice etc. may be consumed by powdering by a blender, or 1 to 4 grains per consumption may be consumed each meal. When the subject is accustomed to meals as grains, it may be gradually increased to 1 meal of uncooked brown rice per day.

Example 1

Increase in blood sugar level when consuming cooked rice consisting of brown rice and uncooked brown rice and cooked rice of conventional white rice were measured.

As a comparative example, blood sugar level and insulin was measured after consumption of 100 grams of white rice, brown rice, and uncooked brown rice at 10 A.M. on an empty stomach. The results of changes measured after several tens of minutes were as follows.

TABLE 4

| Time | Before Meal | 30 minutes post meal | 60 minutes post meal | 90 minutes post meal | 120 minutes post meal |
|---|---|---|---|---|---|
| | White rice | | | | |
| Blood sugar level (mg/100 g) | 103.1 | 137.3 | 142.8 | 140.6 | 129.3 |
| Insulin (μU/ml) | 4.3 | 17.8 | 22.4 | 24.7 | 23.5 |
| | Brown rice | | | | |
| Blood sugar level (mg/100 g) | 101.6 | 138.1 | 152.6 | 139.4 | 120.6 |
| Insulin (μU/ml) | 4.6 | 22 | 22.5 | 23.1 | 18.4 |
| | Uncooked brown rice | | | | |
| Blood sugar level (mg/100 g) | 97.8 | 121 | 126 | 115.5 | 107.4 |
| Insulin (μU/ml) | 4.1 | 12.5 | 12.1 | 11.1 | 9.1 |

As is seen, decrease in blood sugar level was seen with uncooked brown rice.

According to this, Increase in blood sugar level and significant increase in insulin were hardly seen with uncooked brown rice.

Example 2

One hundred grams of uncooked sprouted brown rice was powdered in a blender, consumed as is, or is consumed by seasoning with salt.

Example 3

In cultivation of food such as the brown rice used in the health food of the present invention, a comparative experiment between a cultivation in soil using conventional chemical fertilizer or organic fertilizer and a cultivation in soil using the above described Aquagen seed (the registered trademark of Nihon Pack Co.) was carried out.

Case 1

In soil applied with chemical fertilizer or agricultural chemical necessary for ordinary plants, approximately 65 rice plants/3.31 m² were planted, and cultivated using temporary disease and pest control.

Due to dense planting, photosynthesis was insufficient and irregular rice was prone to be produced. As a result, a well-balanced meal was necessary when consuming this rice.

Case 2

In a soil having high quality with high concentration of amino acids, amount of organic fertilizer necessary for plant growth using Aquagen seed, and for cultivation without agricultural chemicals, approximately 30 to 40 plants/3.31 m² were planted. Photosynthesis became active, irregular rice were less prone to be produced, and the plants were more resistant to damages by disease and pest. Lactic acid bacteria etc. including aerobic microzyme (bacteria, Actinomyces, yeast, and filamentous bacteria) in soil are generated, the amount of yeast increased, higher alcohols were produced, low molecular nutrients were absorbed, and amino acid concentration increased. Plants with residual nitrogen of 300 mg or less were cultivated.

Case 3

Samples of malted rice (koji) were produced by adding "strengthen unrefined-soy-sauce (moromi)" as a seed bacterium into the following crops.

|  | Ratio of extraction (V/W) |
|---|---|
| Rokkaku-reishi mushroom | 12 |
| Ancient Black Rice | 6 |
| Rice according to the present invention | 6 |

These samples of malted rice (koji) were fermented in separate culture vessels and an experiment in prevention activity of malted rice (koji) to diabetic complications, such as diabetic retinitis, diabetic nepfritis or neurosis, was made. A ratio of aldose reductase (AR) inhibitory activity was measured as an index showing prevention activity.

The four extraction solvents below were prepared for the samples.

A: phosphate buffer solution
B: ethanol
C: methanol
D: phosphate buffer solution processed in boiling bath for five minutes Table 5 shows AR inhibitory activity of each sample measured using these extraction solvents.

The ratio of inhibitory activity (%)=[1−($A0$−$A1$)/($C0$−$C1$)]×100

(wherein, A0: absorbance of sample before enzyme reaction, A1: absorbance of sample after enzyme reaction, C0: absorbance of control before enzyme reaction, C1: absorbance of control after enzyme reaction)

These data have shown that AR inhibitory activity of Rokkaku-reishi mushroom in ethanol solvent was high since the extraction density thereof was twice. However, those in other solvents were not high. On the other hand, AR inhibitory activity of the rice (Aquagen rice) cultivated in the soil according to the present invention was very high as compared with other samples. Especially, a remarkable effect of AR inhibitory activity in phosphate buffer solution was identified.

Further, "An experiment in an anti-cancer effect of aldose reductase (AR)" was made.

The samples were left in water twenty-four hours and steamed for forty minutes at 110° C. After the samples were fermented with unrefined-soy-sauce (moromi)" as a seed bacterium for forty-five hours, they were dried and preserved at low temperature. These preserved samples were diluted with phosphate buffer solution (potassium phosphate) into twice or fifth times and kept in refrigerator at 4° C.

After separating enzyme using a filter, samples were passed through a dialysis membrane to obtain small-sized molecular.

Since protein can be passed through an ionization membrane, protein having molecular weight of 500-1000 was obtained.

|  | α-A | G-A | A-P | ACP |
|---|---|---|---|---|
| Aquagen rice (the present invenmtion) | 1941 | 207 | 10034 | 15647 |
| Ancient Black Rice | 286 | 28 | 4161 | 4088 |
| Mushroom | 364 | 20 | 422 | 770 |

α-A: quantity of alpha-amylase (for liquefaction)(cutting off starch)
G-A: quantity of glucoamylase (for saccharification)
A-P: quantity of acidity protease (decomposing amino acid protein)
ACP: quantity of acidity carboxypeptitase (sizing down amino acid)

The experiment shows that Aquagen rice cultivated in soil according to the present invention contains many enzymes in quantity.

INDUSTRIAL APPLICABILITY

The health food of the present invention does not require heat and electricity costs, does not undergo processing treatment of cereals, millets etc., and is trouble-free because it is consumed raw. When it is difficult to consume raw, it can be easily consumed by powdering it and mixing it together with water as juice or soup.

The invention claimed is:

1. A soil, comprising, per 100 g of the soil,
0.02 to 50 mg of amino acid nitrogen, denoted by "A-N",
0.02 to 70 mg of a nitrogen content in one chemical form different from the amino acid form, denoted by "N-N",
2 to 400 mg of phosphate in available form,
1 to 300 mg of exchangeable potassium,
50 to 1000 mg of exchangeable lime,
5 to 400 mg of exchangeable magnesia,
0.5 to 70 ppm of available manganese,
1.5 to 300 ppm of available iron,
0.1 to 30 ppm of available copper,
1.5 to 80 ppm of available zinc,
0.5 to 30 ppm of boron,
0.002 to 2 ppm of molybdenum, and
1.0 to 9.0% of humus, and
wherein the soil has an absorbance index of phosphate of 40 to 3000 mg, a capacity of base substitution of 5 to 40 CEC, an acidity of 3.2 to 7.5 in pH, and an electric conductivity of 0.02 to 5, denoted by "mS/cm".

2. The soil according to claim 1, further comprising a naturally occurring leaf mold.

3. The soil according to claim 1, wherein fungi, microorganisms or insects can coexist with a food chain in the soil, and wherein the soil further comprises an organic fertilizer.

4. The soil according to claim 1, wherein the soil comprises, per 100 g of the soil,
0.3 mg of A-N,
0.7 mg of N-N,
15 mg of phosphate in available form,
15 mg of exchangeable potassium,
200 mg of exchangeable lime,
35 mg of exchangeable magnesia, 5 ppm of available manganese,
15 ppm of available iron,
1 ppm of available copper,
10 ppm of available zinc,
2 ppm of boron,
0.05 ppm of molybdenum, and
wherein the soil has an absorbance index of phosphate of 500 mg, an acidity of 5.5 in pH, and an electric conductivity of 0.05 mS/cm.

5. A method for cultivating a residual-nitrogen-reduced crop comprising growing the crop in the soil according to claim 1.

6. The method according to claim 5, wherein the crop is selected from the group consisting of rice with or without husk, cereals with or without husk, millets with or without husk, pulses with or without husk, tubers, leaf vegetables, fruit vegetables, citrus fruits, melons, fruits and root vegetables.

7. The method according to claim 5, wherein the crop is subjected to at least one treatment selected from the group consisting of radiation of far infrared rays, dispersion of powders of tourmaline, magnesium or chitosan, and dispersion of mature fermented organic matter.

8. The method according to claim 5, wherein the crop is subjected to at least one treatment selected from the group consisting of sterilization by ultraviolet rays, reinforcement of vitamin D by ultraviolet ray, irradiation, pressure treatment by oxygen pressure or nitrogen pressure, temperature treatment by storing in soil or water of 5 to 10 degrees Celsius, heat conduction treatment to a degree that cells of the crop are not destructed, bactericidal treatment, fermentation treatment, biotreatment, solid treatment, fluid treatment, gas treatment, and supercritical treatment.

9. A method for cultivating a residual-nitrogen-reduced crop comprising growing the crop in the soil according to claim 4.

10. The method according to claim 9, wherein the crop is selected from the group consisting of rice with or without husk, cereals with or without husk, millets with or without husk, pulses with or without husk, tubers, leaf vegetables, fruit vegetables, citrus fruits, melons, fruits and root vegetables.

11. The method according to claim 9, wherein the crop is subjected to at least one treatment selected from the group consisting of radiation of far infrared rays, dispersion of powders of tourmaline, magnesium or chitosan, and dispersion of mature fermented organic matter.

12. The method according to claim 9, wherein the crop is subjected to at least one treatment selected from the group consisting of sterilization by ultraviolet rays, reinforcement of vitamin D by ultraviolet ray, irradiation, pressure treatment by oxygen pressure or nitrogen pressure, temperature treatment by storing in soil or water of 5 to 10 degrees Celsius, heat conduction treatment to a degree that cells of the crop are not destructed, bactericidal treatment, fermentation treatment, biotreatment, solid treatment, fluid treatment, gas treatment, and supercritical treatment.

\* \* \* \* \*